(12) United States Patent
Konrath et al.

(10) Patent No.: US 7,718,380 B2
(45) Date of Patent: May 18, 2010

(54) METHOD OF TACROLIMUS EXTRACTION AND QUANTIFICATION USING AQUEOUS DETERGENTS

(75) Inventors: John G. Konrath, Lake Villa, IL (US); David H. Wilson, Zion, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/463,520

(22) Filed: May 11, 2009

(65) Prior Publication Data

US 2009/0275062 A1 Nov. 5, 2009

Related U.S. Application Data

(62) Division of application No. 11/249,188, filed on Oct. 13, 2005, now Pat. No. 7,575,875.

(51) Int. Cl.
*G01N 33/53* (2006.01)

(52) U.S. Cl. .......................... 435/7.1; 435/2; 436/501; 436/518; 436/522; 422/50; 422/61

(58) Field of Classification Search ....................... None
See application file for complete search history.

(56) References Cited

U.S. PATENT DOCUMENTS

| 5,650,288 A | 7/1997 | MacFarlane et al. |
| 6,187,547 B1 | 2/2001 | Legay et al. |

FOREIGN PATENT DOCUMENTS

| WO | 00/05007 | 8/2000 |

OTHER PUBLICATIONS

Alak, A.M., "Measurement of tacrolimus (FK506) and its metabolites: a review of assay development and application in therapeutic drug monitoring and pharmacokinetic studies", Therapeutic Drug Monitoring, vol. 19, No. 3, pp. 338-351, Jun. 1997.
Annesley, Thomas, et al., "Simple Extraction Protocol for Analysis of Immunosuppressant Drugs in Whole Blood", Clinical Chemistry, vol. 50, pp. 1845-1848 (2004).
Chen, Y.L., "Simultaneous determination of three isomeric metabolites of tacrolimus (FK506) in human whole blood and plasma using high performance liquid chromatography-tandem mass spectrometry", J. Chromatogr. B Analyt. Technol. Biomed Life Sci., vol. 830 (2), pp. 330-341, (Jan. 2006).
Gilson ASPEC™ XL4 Four-Probe SPE System, four pages, (description and product specifications) [http://www.gilson.com/products, printed Nov. 28, 2007].
Handschumacher, et al., "Cyclophilin: A Specific Cytosolic Binding Protein for Cyclosporin A" Science, vol. 226, pp. 544-547.
Lensmeyer, G.L., "Therapeutic monitoring of tacrolimus concentrations in blood: semi-automated extraction and liquid chromatography-electrospray ionization mass spectrometry", Ther. Drug Monit., vol. 23(3), pp. 239-249 (Jun. 2001).
McKeon, et al., "When Worlds Collide: Immunosuppressants Meet Protein Phosphatases", Cell, vol. 66, pp. 823-826 (1991).
Davis, et al. Clinical Biochemistry, vol. 33, No. 1, 2000, pp. 1-6.
MacFarlane, et al., Therapeutic Drug Monitoring, vol. 18, No. 6, 1996, pp. 698-705.
PCT/US2006/040484, International Preliminary Report on Patentability and Written Opinion, mailed Apr. 16, 2008.
Stevens, J.M. et al., "Optimization of Solid Phase Extraction by an Automated Method Development Procedure," 31pages, [http://www.gilson.com/applications, printed Nov. 28, 2007].
Warty, V.S., "FK506 Measurement: comparison of Different Analytical Methods", Ther. Drug Monitoring, vol. 15, pp. 204-208 (1993).
Warty, V., et al., "Tacrolimus analysis: a comparison of different methods and matrices", Ther. Drug Monitoring, vol. 17(2), pp. 159-167 (1995).
Winkler, M., "Comparison of Different Assays for the Quantitation of FK 506 Levels in Blood or Plasma", Ther. Drug Monitoring, vol. 16, pp. 281-286 (1994).
Wong, Steven, "Therapeutic drug monitoring for immunosuppressants", Clinica Chimica Acta, vol. 313, pp. 241-253 (2001).
Material Data Sheets for RIPA Lysis Buffer (Sigma dated Sep. 2003).
Material Data Sheets for RIPA Lysis Buffer (Santa Cruz dated Sep. 30, 2004).
Nonidet P-40 (synonyms).
Koefoed-Nielsen, et al., American Journal of Transplantation, 2002, vol. 2, pp. 173-178.

*Primary Examiner*—Lisa V Cook
(74) *Attorney, Agent, or Firm*—Audrey L. Bartnicki (57) ABSTRACT

The present invention relates to a method of extracting tacrolimus in a test blood sample to use in a tacrolimus quantification assay. The method of the present invention extracts tacrolimus in non-precipitating, non-denaturing aqueous environment, avoiding cumbersome manual pretreatment procedures or the use of organic solvents. The method of the present invention permits full automation of tacrolimus quantification assays.

10 Claims, 5 Drawing Sheets

FIGURE 1

Dose-response of semi-automated tacrolimus assay performed on the Abbott ARCHITECT analyzer using bile salt extraction

FIGURE 2

Dose-response of fully automated tacrolimus assay performed on the Abbott IMx analyzer using bile salt extraction

FIGURE 4

Dose-response of fully automated tacrolimus assay performed on the Abbott IMx analyzer using different biles salts for extraction

FIGURE 5

METHOD OF TACROLIMUS EXTRACTION AND QUANTIFICATION USING AQUEOUS DETERGENTS

RELATED APPLICATION INFORMATION

This application is a divisional application of U.S. patent application Ser. No. 11/249,188 filed on Oct. 13, 2005 (now allowed U.S. Pat. No. 7,575,875), which is incorporated by reference in its entirety.

TECHNICAL FIELD

The present invention relates to a simple method of extracting tacrolimus from a test sample for use in a fully automated tacrolimus quantification assay. The method is based on the use of water-soluble detergents.

BACKGROUND

Tacrolimus (also known as ProGraf® and FK506) is a macrolide lactone antibiotic with potent immunosuppresive properties isolated from the soil fungus *Streptomyces tsukubaensis*. Tacrolimus exhibits its immunosuppressive effect by inhibiting the calcineurin pathway (which ultimately inhibits T-cell proliferation) through the formation of a pentameric complex between tacrolimus, FK binding protein (FKBP), calmodulin, and calcineurins A and B (McKeon et al., *Cell Vol.* 66, pages 823-6 (1991)). Tacrolimus binds tightly to FKBP (Kd~0.4 nM), and is also known to bind to cyclophilin (Handschumacher et al., *Science Vol.* 226, pages 544-547 (1984)), albumins, and alpha-1-acid glycoprotein (Wong, *Clinica Chimica Acta Vol.* 313, pages 241-253 (2001). Tacrolimus, used in combination with other immunosuppressants, has gained broad acceptance for the treatment of tissue rejection following organ transplantation.

Extreme inter-patient variability between drug dosage and drug blood levels leads to its potential for toxicity, making therapeutic monitoring of tacrolimus levels in patients undergoing tacrolimus immunosuppressive therapy a standard practice.

Tacrolimus is extensively sequestered in erythrocytes (red blood cells or RBCs), bound to FK binding protein (FKBP; therefore, whole blood samples are a preferred matrix for therapeutic blood monitoring of tacrolimus, even if it can be extracted form biopsies samples, bone marrow and other body fluids. Tacrolimus also forms complexes with other blood plasma constituents such as immunophilins, albumin and lipoproteins. In order to determine the presence of tacrolimus and its concentration in a human blood sample, RBC's present in the sample must be lysed to release the tacrolimus/protein complexes. Then the tacrolimus/protein complexes must be dissociate to release tacrolimus.

Tacrolimus has limited solubility in aqueous solutions. Consequently, all available tacrolimus assays use organic solvents to extract the drug for assay. Organic solvents (eg., ethyl-acetate, methanol, methylene chloride) have been used routinely to lyse the red blood cells, to denature proteins and to extract tacrolimus in preparation for its quantification.

The use of organic solvent-based procedures suffer form several significant disadvantages. For example, organic solvents are highly volatile, highly flammable, and involve hazardous materials that must be properly disposed of in accordance with environmental guidelines.

The volatility of organic solvents can also interfere with accurate quantification of tacrolimus on account of the accumulative evaporation of the volatile solvents. Excessive evaporation at each step of extraction, and during sample assay incubations, can result in the detection of artificially elevated levels of tacrolimus.

All current procedures for tacrolimus extraction require a complex manual sample preparation. Current procedures require a sample denaturation/extraction step, a centrifugation step and a supernatant decantation step. Currently used manual tacrolimus extraction procedures are slow, labor intensive processes. They typically involve precision pipetting of four components: the sample, the denaturant agent, the extraction agent and the extracted sample. Manual precision pipetting is time consuming and potentially unreliable. Consequently these procedures are expensive in terms of the costs associated with staffing. They are also technically limited in terms of analytical throughput and tacrolimus quantification accuracy.

The use of organic solvents along with denaturation, centrifugation, and decantation steps, required with current sample pretreatment procedures preclude the full automation of tacrolimus quantification assay. For full automation of quantification to be possible, all of the reagents and samples must remain in an aqueous form. Denaturation (lysis) and centrifugation of the blood sample would no longer be required. The use of aqueous solutions would also eliminate the excessive evaporation effects, and the risks associated with the use of volatile, flammable, potentially explosive conditions in an electrical device.

Accordingly, there is a need for and interest in the art of devising a fully automated method for tacrolimus quantification that eliminates the need for elaborate and cumbersome sample pretreatment. Such a method would represent a considerable improvement over current methods known in the art in terms of cost per test. The elimination of the manual interaction of the user with the samples would also improve method reproducibility by eliminating human errors, which can affect the drug extraction (and hence, the subsequent result).

The present invention provides a method of extracting tacrolimus in a non-precipitating, non-denaturing aqueous environment, which not only eliminates the use of organic solvents and centrifugation, but also fulfills the requirements for full automation of tacrolimus quantification assays.

DETAILED DESCRIPTION OF THE INVENTION

The present invention provides a non-precipitating, non-denaturing aqueous method for tacrolimus extraction, which permits a fully automated method of tacrolimus quantification in a test blood sample without the need of manual pretreatment.

Because tacrolimus is extensively bound to RBCs, the preferred test blood sample is whole blood, although it can be a sample that contains previously washed RBCs.

The method of the present invention comprises mixing the test blood sample with at least one hemolytic agent and at least one tacrolimus extraction agent. The two agents can be added in one step or in separate steps.

The hemolytic agent lyses the red blood cells resulting in the release of the tacrolimus/protein complexes. For the purpose of the present invention, the terms "hemolytic", "erythrocytic" or "erythrolytic" have the same meaning, i.e. disruption of red blood cells resulting in liberation of intracellular contents.

The extraction agent dissociates or releases tacrolimus from its complex with blood protein components into an aqueous solution compatible with subsequent quantification assay methods.

Finally, during the quantification process, the concentration of extracted tacrolimus is determined. In such quantification process the determined concentration of extracted tacrolimus corresponds to the concentration of tacrolimus originally present in the blood sample.

Because full automation of Tacrolimus extraction and quantification requires that there be no removal of any component from the sample/lysis/extraction mixture prior to assay, the hemolytic agent must exhibit powerful erythrocytolytic activity, and yet not denature the antibodies or other receptor molecules needed in the quantification assay. Similarly, the concentration of the hemolytic agent must be sufficient to lyse any cellular membranes in the sample almost immediately, and at the same time must not interference with the tacrolimus quantification process. Hemolytic agents that can be used in the method of the present invention may include non-ionic detergents, or low ionic strength (or ion-free) aqueous solutions, for example water. These agents are known for strong erythrocytic properties through osmotic shock (hypotonic disruption).

As stated above, when a detergent is used as the hemolytic agent, it must be one whose continued presence in the assay does not interfere with the assay itself. Therefore, strong denaturing ionic detergents such as sodium dodecyl sulfate should be avoided. Preferred detergents include non-ionic detergents, such as octylphenoxy polyethoxyethanol (Triton® X-100), or saponin, preferably Triton® X-100. In addition, for full automation, it is imperative that the detergent maintains solubility of the reaction mixture throughout the binding incubation period of the assay.

In part, because tacrolimus is hydrophobic, it binds to known high-affinity and specific binding proteins present in blood. Immunophilins are an example of high-affinity and specific binding proteins having physiological significance. Immunophillins are a family of intracellular binding proteins that bind to several compounds; two distinct families of immunophilins are presently known: cyclophilins and macrophilins, the latter specifically bind tacrolimus. Extraction of tacrolimus that is tightly bound to immunophilins is not readily accomplished using aqueous solutions. Even though tacrolimus has been extensively investigated and used for immunosuppressive therapy for over 10 years, there are no existing methods for extracting tacrolimus based on the use of aqueous non-denaturing reagents. All methods known in the art utilize organic solvents to denature immunophilins and extract tacrolimus for further quantitative concentration determination. It was unexpectedly discovered that water-soluble detergents with the cyclopentanoperhydrophenantrene (cholesterol) backbone exhibit powerful non-denaturing extraction of tacrolimus. Detergents with a cholesterol backbone useful for their tacrolimus extraction activity include, but are not limited to, anionic bile salts, and zwitterionic detergents, such as CHAPS.

"Bile salt" as used herein means any compound or derivative thereof from the class of steroid molecules produced by the liver or gut bacteria, which exhibit detergent properties. Bile salts that provide conditions for tacrolimus extraction from binding proteins present in a test blood sample may be unconjugated (eg. cholate) or conjugated to another moiety, such as for example, a substituted or an unsubstituted alkyl, alkenyl, or alkynyl moiety, or more preferably unsubstituted $C_1$-$C_{30}$ alkyl, alkenyl, or alkynyl moiety such as for example, taurine (eg., taurocholate) or glycine (eg., glycocholate) or a water-soluble aromatic moiety. Bile salts useful in the context of the present invention include, but are not limited to cholate, deoxycholate, chenodeoxycholate, cholylglycine, chenodeoxycholateglycine, cholyltaurine, chenodeoxycholytaurine, chenodeoxycholic acid, lithocholic acid, sulfocholic acid, sulfolithocholic acid, deoxycholylglycine, sulfolithocholylglycine and ursodeoxycholic acid.

As demonstrated in subsequent examples, these water-soluble bile salts represent a class of molecules that exhibit strong non-denaturing tacrolimus extraction activity. For the purpose of demonstration of the invention, the bile salt deoxycholate has been preferred. However, the extraction activity of other bile salts is also demonstrated. This extraction activity of bile salts has not been previously described or alluded to in the prior art, and no such extraction activity would be known a priori by those skilled in the art. Utilizing this property of bile salts provides the necessary conditions for full automation of tacrolimus quantification assay by (a) obviating the use of hazardous organic chemicals, which would be onerous due to the reasons described above and can be dangerous to use in an electrical instrument, and (b) providing good extraction and solubilization in the presence of competing immunophilins present in a test blood sample.

Zwitterionic detergents, such as CHAPS (3-[(3-Cholamidopropyl)dimethylammonio]-1-propanesulfonate hydrate) and CHAPSO, are non-denaturing detergents able to disrupt nonspecific protein interactions and produce low protein aggregation. The non-denaturing tacrolimus extraction activity of CHAPS is demonstrated in Example 4 (FIG. 5) of the present application.

The extraction agent can optionally be supplemented with a second extraction agent such as a phospholipid or non-detergent sulfobetaine. Suitable phospholipids include but are not limited to naturally occurring phospholipids, and particularly include lecithin (phosphatidyl choline).

Because automation requires that tacrolimus be quantified in the presence of both, the hemolytic agent and the extraction agent, the nature and concentrations of these agents is preferably selected such that significant interference with the quantification process is avoided. For example, these agents preferably are not incompatible with, and more preferably do not interfere with, the analyte binding molecule and the signal generation molecule during the quantification process. For the present invention the term "analyte" is the compound of interest (e.g., tacrolimus). The analyte may be captured or bound by a molecule forming a complex. This analyte-binding molecule may include any protein that binds tacrolimus, for example an antibody, or an immunophilin.

Signal-generating molecules can include, but are not limited to alkaline phosphatase or acridinium.

The chemical properties of the water-soluble detergents having a steroid backbone used in the method of the present invention do not cause significant interference by their continued presence in the assay at concentrations required for extraction.

The test blood sample should be incubated with the hemolytic agent for a time and under conditions sufficient for complete lysis, and more preferably sufficient for the solubilization of cell membranes and components to occur. Suitable times can be from a few seconds to several hours depending on the agent.

Similarly, the sample should be incubated with the extraction agent for a time and under conditions sufficient to allow tacrolimus to be extracted from immunophilins or other binding proteins. These conditions vary according to the chosen concentrations of the detergents and relative volumes of sample. In general, the concentration of detergent should be in the range of about 0.1% to about 3.0% w/v, and preferably about 0.3% to about 1.0%, during the RBC lysis step, and the concentration of extracting agent (deoxycholate or other aqueous detergents) should be in the range of about 0.3% to about 1%, preferably about 0.4% to about 0.6% during the extraction step.

The test blood sample can be brought into contact with the hemolytic agent and the extracting agent in separate steps (hemolytic agent first, followed by bile salt(s)), or in the same step. Because the two agents are usually compatible, the test blood sample is preferably mixed with a solution containing both agents. Incubation time of extraction can be of a wide range depending on the type of assay, it may be only few seconds (e.g., in many quick non-equilibrium immunoassays), to several hours (e.g., in some equilibrium microtiter plate assays). For purposes of automation and reducing processing time, shorter incubation times with the hemolytic agent or extraction agent or both are preferred. Accordingly, incubation times for each step individual or a combined step are preferably 10 to 20 minutes.

Following the hemolysis and the extraction processes, the concentration of tacrolimus in the sample can be determined by any one of a number of methods known to those of ordinary skill in the art. Immunoassays or receptor binding assays (eg., immunophilin receptor assay) can be used. Preferably, an immunoassay is used. For semi or full automation, any of a number of commercially available automated immunoassay analyzers can be used. The immunoassay method would preferably be of the heterogeneous type, which enables capture of tacrolimus onto a solid phase (either through antibody or protein receptors known to bind tacrolimus, such as FKBP) and subsequent separation of potentially interfering components (such as hemoglobin) in the blood test sample from the bound tacrolimus. This includes radioimmunoassay (RIA), enzyme-linked immunosorbant assay (ELISA), microparticle enzyme immunosorbant assay (MEIA), ion-capture assay, chemiluminescent-based assay, or other known and commercially available assay configurations for analyte capture, signal generation, and detection.

Preferred instruments for demonstration of the present invention are the Abbott IMx™ immunoassay analyzer, and the Abbott ARCHITECT™ immunoassay analyzer. Antibodies, preferably monoclonal antibodies, for use in an immunoassay can be obtained in accordance with methods known to those of skill in the art. Antibodies may also be obtained from commercial sources, such as Astellas (Osaka, Japan).

Optimum sample size depends on the quantities that are preferred for the particular method of tacrolimus assay. By way of example, and not limitation, minimum sample volumes in the range of 50-200 •L are often required for immunoassays with sufficient sensitivity for medical diagnostics. Abbott IMx™ and Abbott ARCHITECT™ immunoassay analyzers require minimum sample volumes of 150 •L to achieve optimal sensitivity. This provides sufficient volume for premixing the sample, and yet enough volume to perform a test. Those of ordinary skill in the art will appreciate that aspirated volumes for assay can affect the assay sensitivity. Optimization of the aspirated sample volume would accompany development of any assay for tacrolimus.

The present invention also encompasses a diagnostic test kit, based on the method of the present invention, for the automated or semi-automated quantitative determination of tacrolimus in blood test samples. The kit of the present invention comprises Triton® X-100, as the preferred hemolytic agent, and deoxycholate as the preferred bile salt extracting agent.

In summary, the present invention enables fully automated determination of tacrolimus concentration in blood test samples with a sensitivity and accuracy that is comparable to current methods that require cumbersome manual extraction procedures using organic solvents.

The present invention will be further clarified by the following examples, which are only intended to illustrate the present invention and are not intended to limit the scope of the present invention.

EXAMPLES

Example 1

Figure 1:
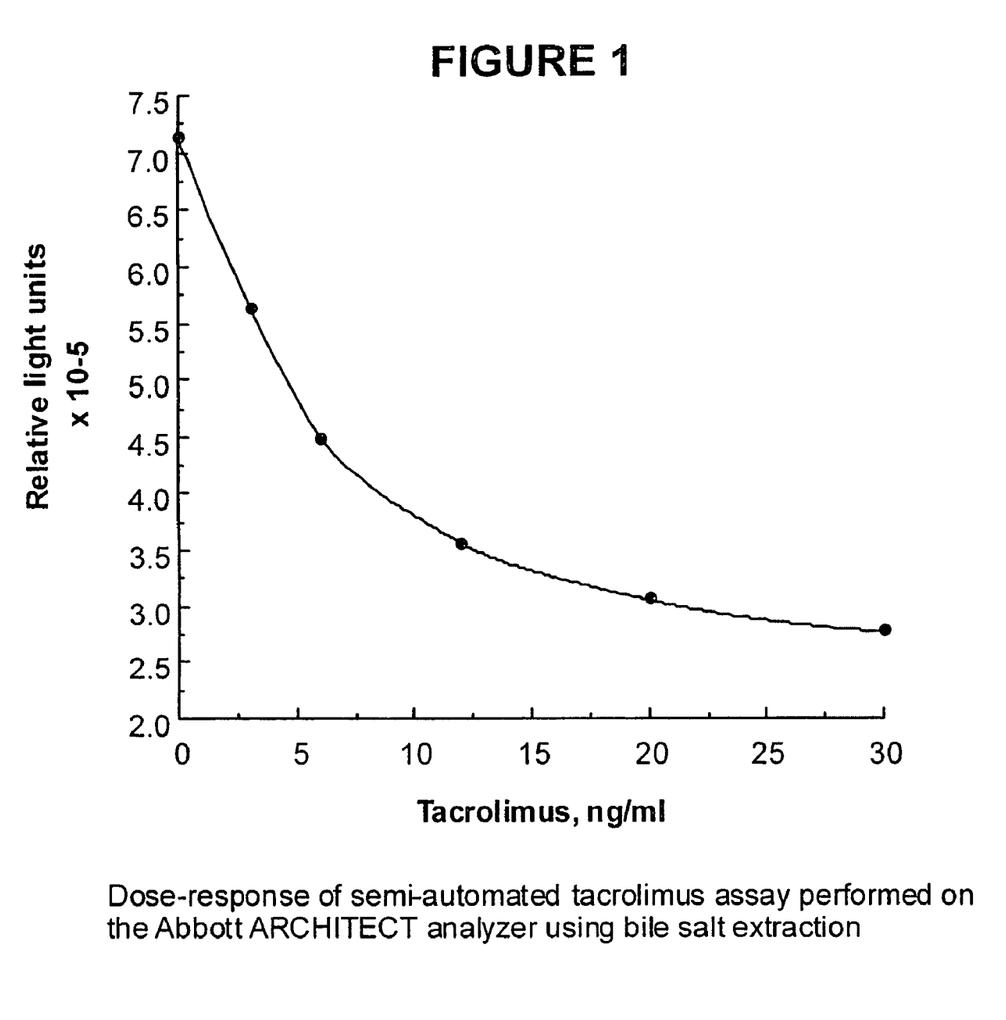
FIG. 1 graphically presents a dose-response curve from a semi-automated tacrolimus assay performed on the ARCHITECT™ analyzer (Abbott Laboratories, Abbott Park, Ill.) using bile salt as the tacrolimus extraction agent.

Use of a Bile Salt to Extract Tacrolimus from Pre-Lysed Human Blood for Quantification by the Abbott ARCHITECT® Immunoassay Analyzer in a Semi-Automated Format Tacrolimus (Fujisawa Pharmaceutical Co., Ltd, Osaka) was added gravimetrically to pre-lysed and filtered human whole blood to provide for a series of six tacrolimus samples for analysis (samples comprised concentrations between 2.5 and 30 ng/mL, and a blank). 110 μL of each sample was pre-mixed with 110 μL of a solution of 0.8% deoxycholate (Sigma, St. Louis, Mo.) in ARCHITECT® sample cups. The mixture was vortexed for 30 seconds for thorough mixing. Reagent bottles containing magnetic microparticles (Polymer Laboratories, Shropshire, England) coated with antibody recognizing tacrolimus and a solution of tracer conjugate of tacrolimus and acridinium (Abbott Laboratories, Abbott Park, Ill.) for light signal generation were placed on board the ARCHITECT® instrument. Following initiation of the run, the ARCHITECT® pipetter transferred 40 μL of each pre-extracted sample to the ARCHITECT® reaction vessel (RV). This was followed by the addition of 50 μL of anti-tacrolimus antibody coated microparticles. The reaction mixture was allowed to incubate for 18 minutes. Following a wash step in which the magnetic microparticles are captured by means of a magnet and then resuspended in the RV in a phosphate buffer, 50 μL of tacrolimus-acridinium tracer were added to each RV and incubated for four minutes. Following a second wash, bound tracer was released, triggered with a peroxide solution, and chemiluminescent light measured in the standard sequence for the ARCHITECT® instrument system. Because this example is a competitive immunoassay, the light signal is inversely proportional to the concentration of tacrolimus in the sample. FIG. 1 shows the relationship between light signal and tacrolimus concentration. The changing signal with tacrolimus concentration indicates that tacrolimus has been extracted from the whole blood matrix, captured by the anti-tacrolimus microparticles, and detected by the tacrolimus-acridinium conjugate. This example demonstrates extraction of tacrolimus from endogenous binding proteins present in a matrix of human whole blood in a non-denaturing aqueous environment using deoxycholate as the extraction agent, and quantification by an automated immunoassay analyzer.

Example 2

Figure 2:
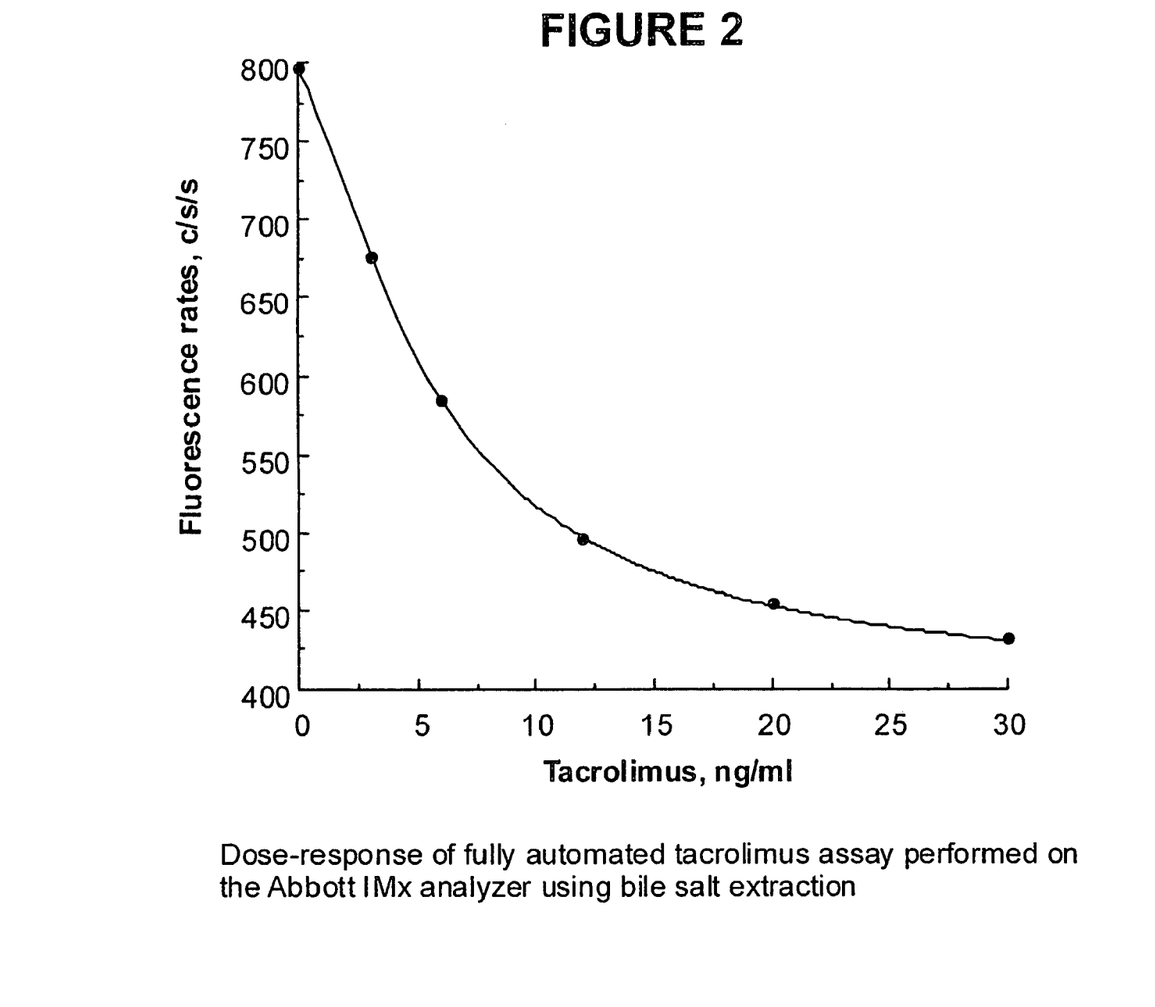
FIG. 2 is a dose-response curve from a fully automated tacrolimus assay performed on the IMx™ analyzer (Abbott Laboratories, Abbott Park, Ill.) using bile salt as the tacrolimus extraction agent.
Figure 3:
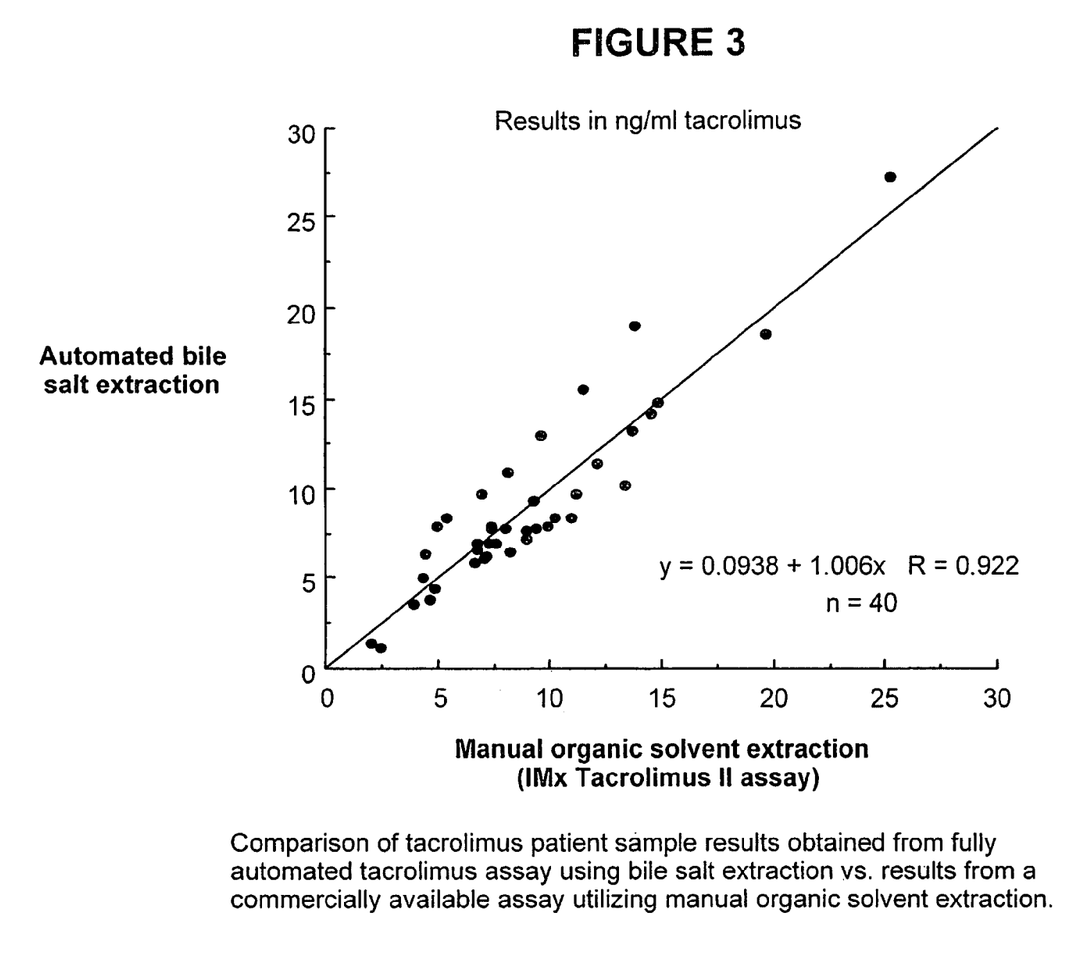
FIG. 3 graphically compares tacrolimus patient sample results from a fully automated assay using bile salt extraction vs. results from a commercially available assay using manual organic solvent extraction.

Full Automation of Tacrolimus Quantification From Whole Blood Patient Samples Using a Bile Salt for Extraction and the Abbott Imx® Immunoassay Analyzer Whole blood from tacrolimus patient samples (150 mL aliquots) were pipetted into the sample wells of separate IMx reaction cells (each cell corresponding to a single patient sample). The accuracies of the pipetted volumes were not important for the outcome, provided that there was sufficient specimen for the Imx® instrument to perform its pipetting operations on the specimen (a minimum volume of 150 uL is recommended in the instrument operation manual). The IMx® carousel containing the IMx® reaction cells loaded with tacrolimus samples was placed in the IMx instrument. A diagnostic kit of four reagents, including an hemolytic/extraction reagent containing 1.0% (V/V) Triton® X-100 and 0.5% (V/W) deoxycholate, was placed on-board the instrument and the fully automated IMx run was initiated. The IMx® probe-electrode assembly first aspirated and dispensed 90 mL of the whole blood samples two times to re-suspend settled RBCs. 80 mL aliquots of hemolytic/extraction reagent were mixed with 80 mL of whole blood from each sample in the pre-dilute wells of IMx® reaction cells by the IMx® probe/electrode assembly. 50 mL of the lysed and extracted samples were transferred to the incubation wells of each IMx® reaction cell along with 50 mL of anti-tacrolimus coated microparticles from a second bottle of the reagent kit and 50 mL of additional hemolytic/extraction reagent. The reaction mixture was allowed to incubate for 30 minutes at 37 C. Following incubation, 175 mL aliquots of reaction mixture from each sample were transferred to the glass fiber matrix of the IMx reaction cells by the Imx® probe-electrode assembly. The reaction cell matrices were washed with two 100 mL aliquots each of hemolytic/extraction reagent to remove sample hemoglobin and other potentially interfering substances from the glass fiber matrix. 70 mL aliquots of a conjugate of alkaline phosphatase and tacrolimus from a third bottle of the reagent kit were then added to the reaction cell matrices by the IMx® probe/electrode assembly and allowed to incubate for 28 minutes. The matrix was then washed with IMx® instrument line buffer (0.3 M NaCl in Tris buffer, 2×100 mL). The IMx® probe/electrode assembly then transferred 70 mL of reporter substrate 4-methylumbelliferyl phosphate (MUP) (Abbott Laboratories, Abbott Park, Ill.) from a forth bottle of the reagent kit to each matrix of the IMx® reaction cells. Immediately following MUP addition, fluorescent product was measured for each sample (in counts per second per second, c/s/s) by the IMx® optical assembly. Fluorescent signal was inversely proportional to the concentration of tacrolimus in the sample. The signal was converted to tacrolimus concentration units automatically using a calibration curve which had been previously stored in the instrument memory. The calibration curve is exhibited in FIG. 2. The calibrators were prepared by gravimetrically adding known quantities of tacrolimus into human whole blood. The tacrolimus concentration results for 40 tacrolimus patient samples are exhibited in FIG. 3 compared with results from a commercially available assay for tacrolimus that requires a manual extraction of the samples with an organic solvent prior to assay. FIG. 3 demonstrated that the fully automated assay using bile salt extraction gave tacrolimus results comparable to or better than a commercially available assay, which requires manual extraction and centrifugation of the sample prior to assay.

Example 3

Extraction Activity of Bile Salts Other than Deoxycholate for Tacrolimus

Figure 4:
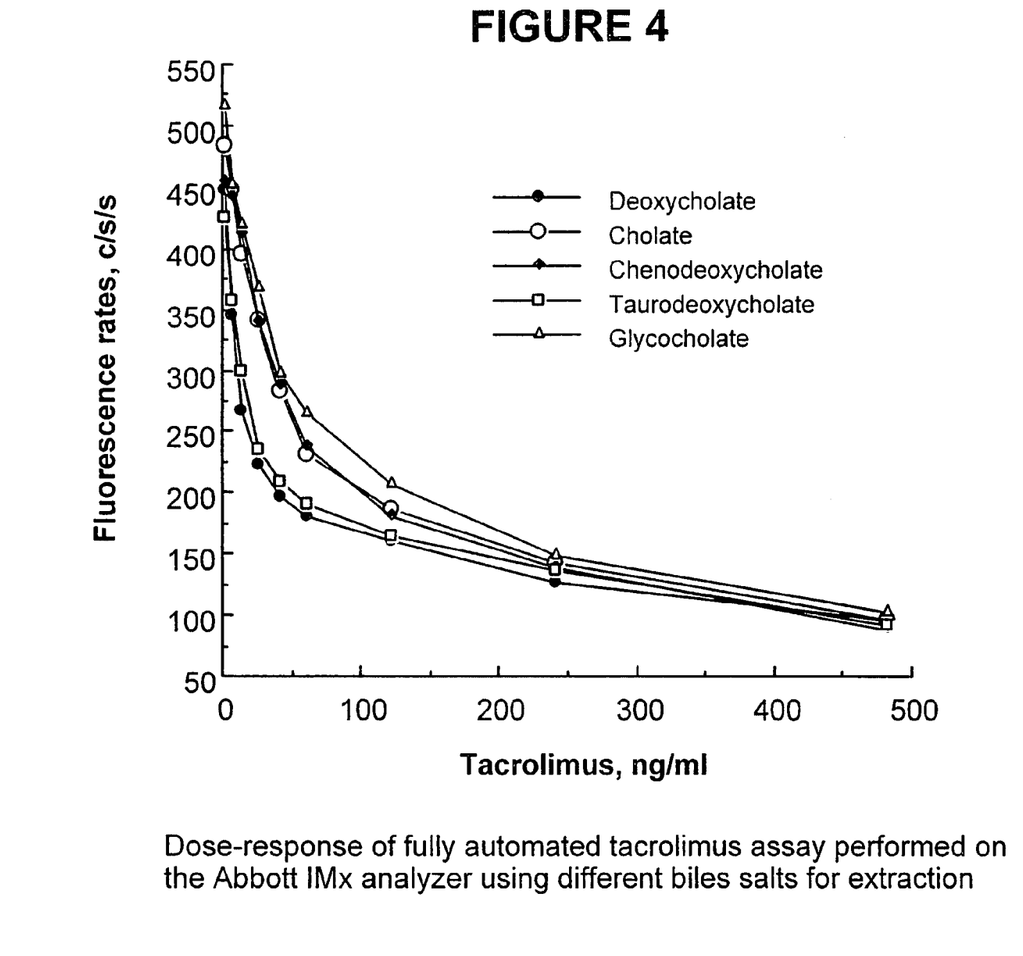
FIG. 4 is a dose-response of a fully automated tacrolimus assay performed on the IMx™ analyzer using five different bile salts for extraction.

Tacrolimus was added gravimetrically to normal whole blood to provide a series of nine whole blood tacrolimus samples (3 to 480 ng/ml, and a blank) for analysis. Five separate hemolytic/extraction reagents were prepared using five different bile salts at a concentration of 0.5%. In addition to 0.5% of each of deoxycholate, cholate, chenodeoxycholate, taurodeoxycholate and glycocholate (Sigma, St. Louis, Mo.), each hemolytic/extraction reagent included 1.0% Triton® X-100 as the hemolytic agent. A bottle of each hemolytic/extraction reagent was added to the diagnostic kit described in Example 2 (anti-tacrolimus coated microparticles, conjugate of alkaline phosphatase (Roche, Basel) and tacrolimus, and MUP). The set of nine prepared whole blood tacrolimus samples were then assayed with each reagent kit using the fully automated assay described in Example 2. FIG. 4 shows inverse dose-response curves obtained from each of the five bile salt examples. All bile salts tested exhibited significant extraction activity for tacrolimus, as indicated by the change in fluorescent signal with tacrolimus concentration.

Example 4

Extraction Activity of Chaps for Tacrolimus

Figure 5:
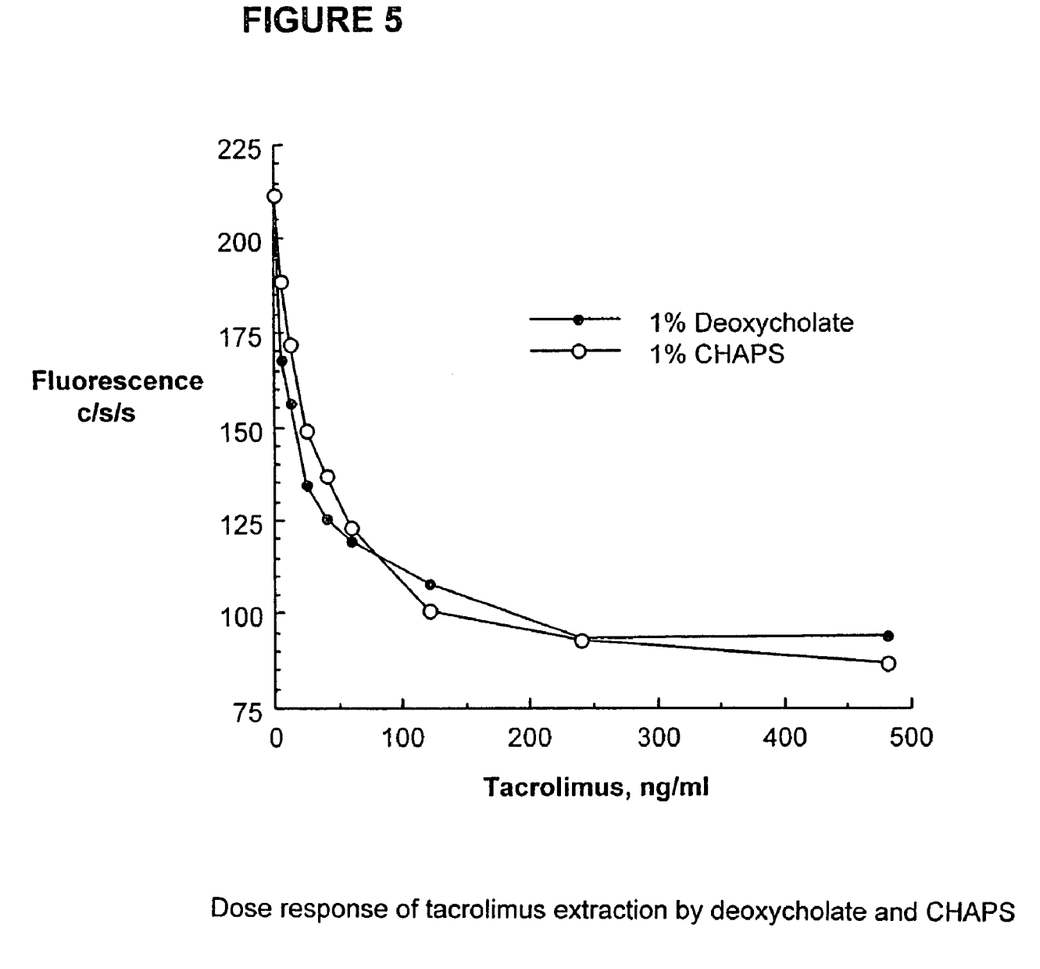
FIG. 5 graphically compares two dose-response of fully automated tacrolimus extraction using deoxycholate and CHAPS on the IMx™ analyzer

Tacrolimus was added gravimetrically to normal whole blood to provide a series of whole blood tacrolimus samples (3 to 480 ng/ml, and a blank) for analysis. Experiments were run as described in previous examples in Tris buffer, using 1% CHAPS as the extracting agent and 0.5% Triton® X-100 as the hemolytic agent. As shown in FIG. 5 there is comparable extraction activity between the two non-denaturing detergents, deoxycholate and CHAPS.

What is claimed is:

1. A method of extracting tacrolimus from a blood sample, comprising contacting the blood sample with a non-ionic detergent hemolytic agent and a water soluble detergent extraction agent, wherein said hemolytic agent is octylphenoxy polyethoxyethanol and said extraction agent is a zwitterionic bile salt detergent.

2. The method of claim 1 wherein the blood sample is provided in a non-denaturing aqueous environment.

3. A method of determining tacrolimus concentration in a test blood sample in a non-denaturing aqueous environment, comprising the processes of:
   (a) mixing a test blood sample with a non-ionic detergent hemolytic agent and a water soluble detergent extraction agent, wherein said hemolytic agent is octylphenoxy polyethoxyethanol and said extraction agent is a zwitterionic bile salt detergent,
   (b) lysing said blood sample by said hemolytic agent,
   (c) extracting tacrolimus by said water soluble extraction agent, and (d) determining tacrolimus concentration in said blood sample in an automated system, wherein the determined concentration of extracted tacrolimus corresponds to the concentration of tacrolimus present in said blood sample.

4. The method of claim 3 wherein the method of determining tacrolimus concentration in the sample is by an immunoassay.

5. The method of claim 3 wherein the method of determining tacrolimus concentration in the sample is by immunophilin receptor binding assay.

6. The method of claim 4 wherein the immunoassay method is selected from the group consisting of radioimmunoassay (RIA), enzyme-linked immunosorbant assay (ELISA), microparticle enzyme immunosorbant assay (MEIA), ion-capture assay, and chemiluminescent-based assay.

7. An assay kit suitable for detecting the level of tacrolimus in a human whole blood sample using an automatic system, said kit comprising a non-ionic detergent hemolytic agent and a water-soluble detergent extraction agent, wherein said hemolytic agent is octylphenoxy polyethoxyethanol and said extraction agent is a zwitterionic bile salt detergent.

8. The assay kit of claim 7, wherein the zwitterionic bile-salt detergent is 3-[(3-Cholamidopropyl)dimethylammonio]-1-propanesulfonate hydrate.

9. The assay kit of claim 7, wherein said assay kit can be used in a semi-automated assay platform.

10. The assay kit of claim 7, wherein said assay kit can be used in an automated assay platform.

* * * * *